United States Patent [19]

Lowin et al.

[11] Patent Number: 4,636,202

[45] Date of Patent: Jan. 13, 1987

[54] MEDICAMENT APPLICATOR WITH PLUNGER ASSEMBLY AND AUTOMATICALLY-OPENABLE CLOSURE THEREFOR

[75] Inventors: David A. Lowin, Woodside; Richard A. Fayram, Palo Alto; Andrew J. Bivetto, Los Gatos, all of Calif.

[73] Assignee: Syntex (U.S.A.) Inc., Palo Alto, Calif.

[21] Appl. No.: 635,334

[22] Filed: Jul. 27, 1984

[51] Int. Cl.⁴ ......................................... A61M 31/00
[52] U.S. Cl. ..................... 604/236; 604/218; 604/228; 604/16; 604/187; 222/493
[58] Field of Search ............... 604/218–235, 604/236, 238, 275, 279, 192, 263, 38–40, 150, 90, 198, 15, 16, 18, 33, 249; 222/491–494, 387

[56] References Cited

U.S. PATENT DOCUMENTS

| | | | |
|---|---|---|---|
| 1,987,156 | 1/1935 | Paparello | 222/494 |
| 2,072,327 | 3/1937 | Friedman et al. | 128/234 |
| 2,178,840 | 11/1939 | Lorenian | 128/260 |
| 2,185,536 | 1/1940 | Borland et al. | 604/218 |
| 2,587,984 | 3/1952 | Edwards | 604/218 |
| 2,691,982 | 10/1954 | Jones | 128/261 |
| 2,720,881 | 10/1955 | Jones | 128/261 |
| 2,767,712 | 10/1956 | Waterman | 604/187 |
| 2,893,390 | 6/1959 | Lockhart | 604/238 |
| 3,115,135 | 12/1963 | Sarnoff | 604/228 |
| 3,506,008 | 4/1970 | Huck | 128/261 |
| 3,572,337 | 5/1971 | Schunk | 604/227 |
| 3,586,068 | 6/1971 | Nicolson | 222/494 |
| 4,225,062 | 9/1980 | Sneider | 604/215 |
| 4,267,846 | 5/1981 | Kontos | 604/220 |
| 4,390,016 | 6/1983 | Reiss | 604/236 |
| 4,411,647 | 10/1983 | Sakurai et al. | 604/16 |

Primary Examiner—C. Fred Rosenbaum
Assistant Examiner—Karen L. Kaechele
Attorney, Agent, or Firm—David A. Lowin; John A. Dhuey

[57] ABSTRACT

A compact, prefilled, ready-to-use, applicator for dispensing a medicament within a body cavity has a reservoir, an automatically-opening closure member and a telescoping plunger assembly. A closure member is disclosed, adapted to open responsive to the pressure of a medicament being dispensed, without disengaging from the reservoir in which the medicament is contained. A telescoping plunger assembly is disclosed, having impeller means disposed within the reservoir opposite the cap member and engaging means to lock the assembly in an extended position for urging the impeller means through the reservoir.

30 Claims, 17 Drawing Figures

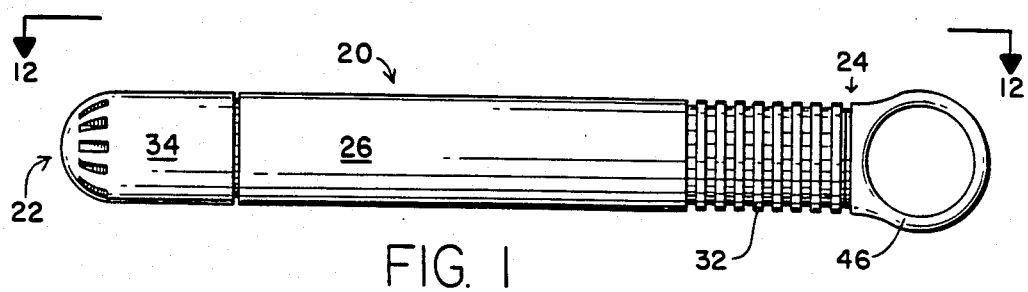
FIG. 1
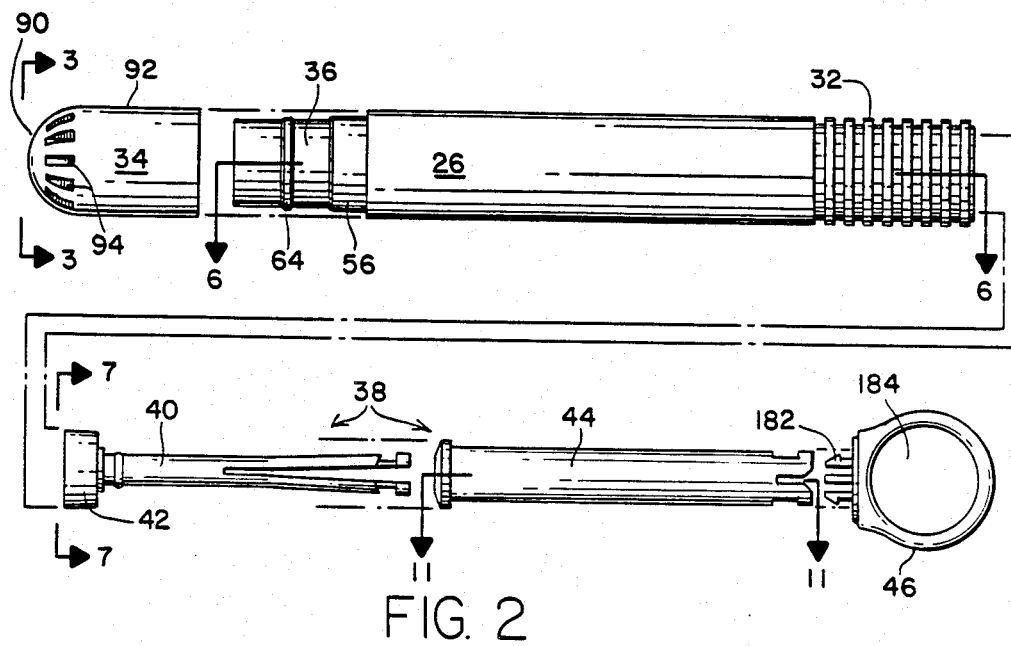
FIG. 2
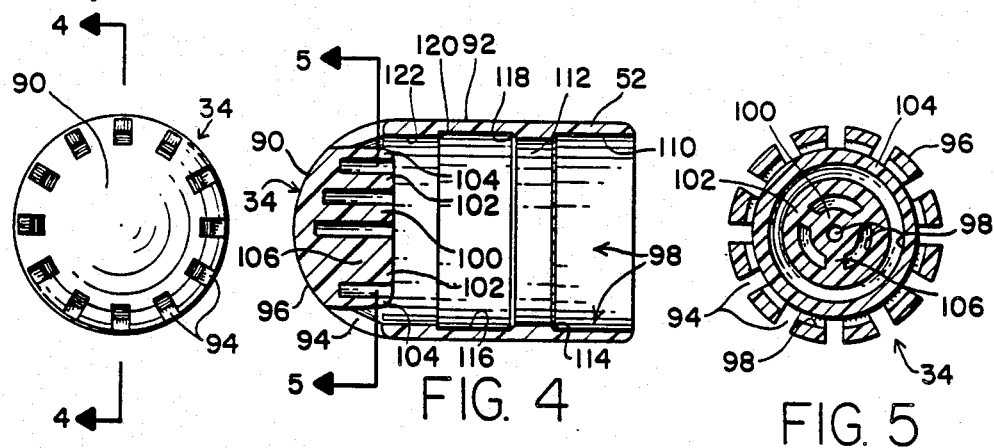
FIG. 3
FIG. 4
FIG. 5

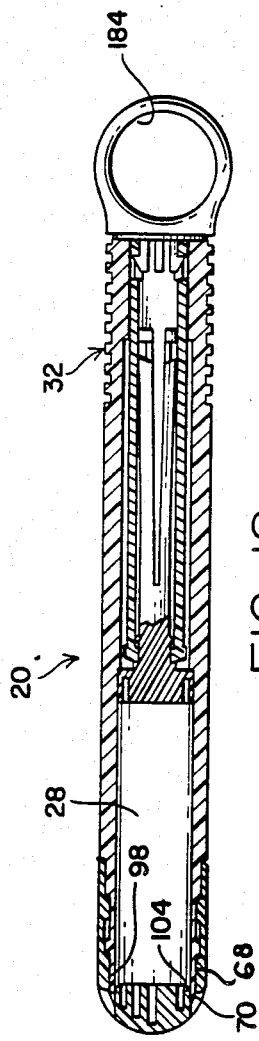
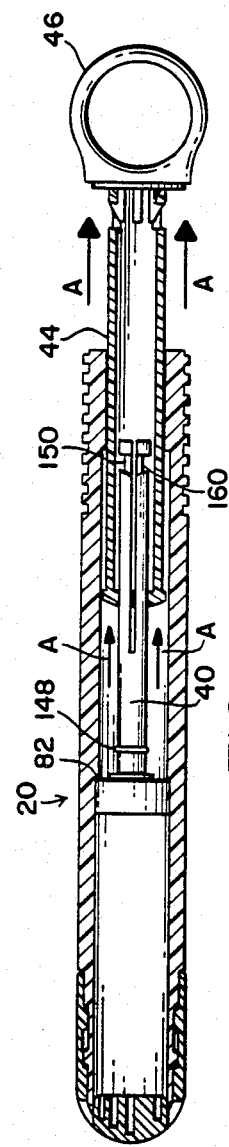
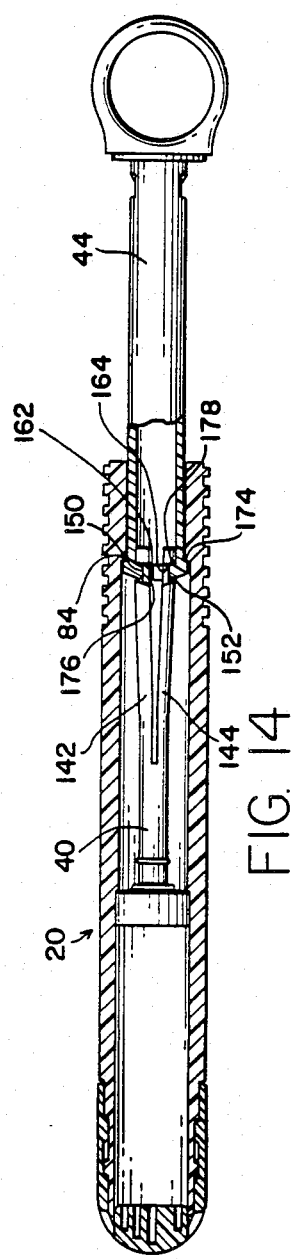
FIG. 12
FIG. 13
FIG. 14

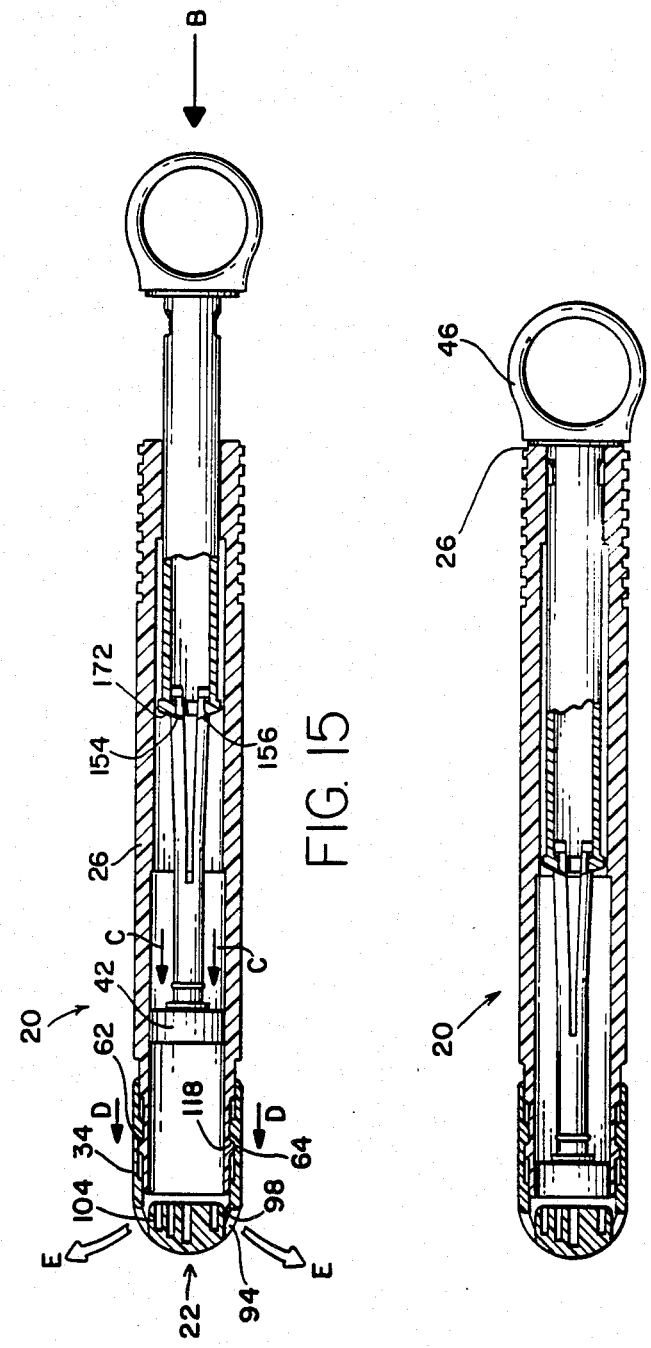

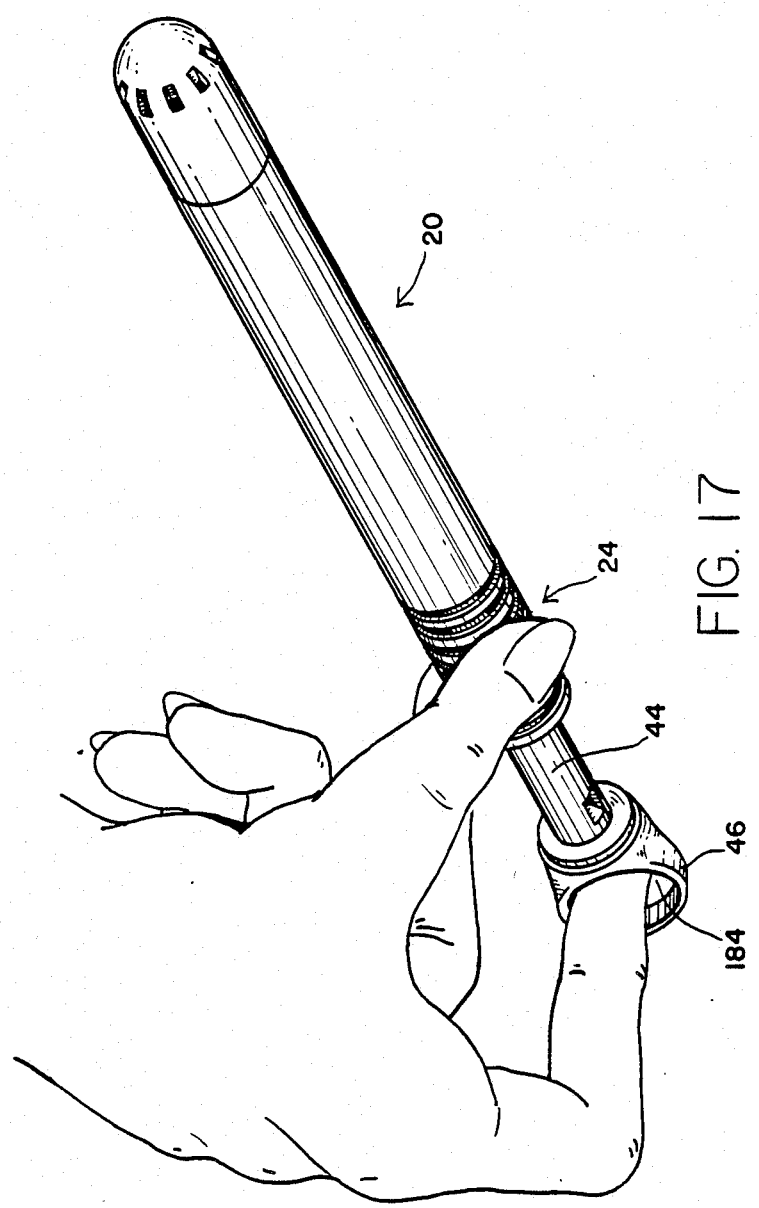

MEDICAMENT APPLICATOR WITH PLUNGER ASSEMBLY AND AUTOMATICALLY-OPENABLE CLOSURE THEREFOR

FIELD OF THE INVENTION

The present invention relates to medicament applicators, particularly to applicators for insertion into a bodily orifice and for the delivery of a medicament to the area therein, and specifically to an applicator for delivering a medicament within the vagina.

BACKGROUND OF THE INVENTION

In the past, there have been two principal methods and means for delivering a medicament within a body cavity, namely squeezable reservoir-type applicators and syringe-type applicators. The squeezable reservoir-type applicators suffer from several drawbacks in that they are often cumbersome, difficult to handle, imprecise at delivering a measured dosage, and inefficient because there is usually a significant amount of medicament remaining in the reservoir after use. Likewise, syringe-type applicators are typically somewhat bulky, difficult to use, and oftentimes inefficient in that a significant amount of medicament remains in the syringe after use.

The present invention pertains more to the syringe-type class of medicament applicators. These applicators have typically included a tubular reservoir with a delivery portion and closure at one end and a piston and rod (or plunger) at the other end. Following are some examples of syringe-type applicators of the past.

The U.S. Patent to Lorenian (U.S. Pat. No. 2,178,840) discloses a cylinder cut to have the shape of saw teeth at one end, which teeth are then bent toward the cylinder's central axis until they meet and thereby provide a closure, such that when acted on by pressure applied to dispense the medicament, the saw teeth part, clearing the way for the medicament.

U.S. Pat. No. 2,720,881 (to Jones) illustrates different forms of pressure-actuated, automatically-opening closures for the end of a medicament applicator. There, the closure is formed as part of a flat end of a crushable container held inside the applicator tube. The closures are varied designs of light incisions into the face of the flat end. These forms of closure are likely to be somewhat air-permeable, do not have the structural strength to serve as a contoured insertion tip for the applicator, and are subject to being accidentally opened.

A different form of disposable applicator is shown in another U.S. Patent to Jones (U.S. Pat. No. 2,691,982) wherein, for compactness purposes, the plunger is a hollow tube with a crimped end and an open end. The open end is disposed within the barrel of the applicator, surrounding a crushable thin-walled container at the delivery end of the applicator tube. For use, the plunger is removed, inverted, reinserted (crimped end first) into the tube and applied against the thin-walled collapsible container to expel the medicament through a discharge opening at the end of the applicator, which opening is forced open by the pressure of the medicament. This device is difficult to use, in that it involves disassembly and reassembly, and is not tapered for easy insertion. The closure portion suffers form the disadvantages discussed above with reference to U.S. Pat. No. 2,720,881.

The U.S. Patent to Huck (U.S. Pat. No. 3,506,008) provides a reservoir with a tapered dispensing end and a cap receivable over the tapered end to serve as a closure, requiring complicated internal threading to secure the closure in place. The cap is removable by twisting it off, and then must be inverted and inserted into the other, larger end of the dispenser, were it is used as a rod to drive a piston down the barrel of the applicator to expel the medicament contained therein. The Huck device likewise suffers from being difficult to use.

As a final example of prior applicators, in the U.S. Patent to Friedman, et al. (U.S. Pat. No. 2,072,327) a dispensing device is shown wherein a syringe has a piston with a rod disposed therethrough. An enlarged end of the rod mates with an opening at the delivery end of the syringe barrel and acts as a closure therefor. In use, the rod is drawn back, thereby opening the dispensing orifice, and pulled back towards the opposite end of the applicator, passing through the piston until the enlarged end of the rod comes into a locking engagement with the piston. So engaged, the rod can be used to move the piston through the syringe towards the dispensing end, thereby expelling the medicament. This device, while providing a reasonably compact medicament applicator, suffers from problems in sealing (to prevent moisture evaporation from the medicament) and apparently also from difficulty in use because the plunger stem resists being drawn back and does not have an easy-to-use grasping surface. The device would be difficult to prefill with medicament, and further, medicament appears likely to adhere to the sides of the rod when it is drawn back through the medicament in order to be set into the piston for discharge.

These disadvantages have all been overcome in the present invention, which can be described as having the following aspects.

ASPECTS OF THE INVENTION

One aspect of the present invention is to provide a compact medicament applicator.

Another aspect of the invention is to provide a medicament applicator that can be held and operated using only one hand.

Still another aspect of the invention is to provide a medicament applicator having an automatically-opening dispensing end that provides a moisture-loss-inhibiting, product retaining seal.

A still further aspect of the invention is to provide a medicament applicator having an easy-to-use plunger assembly that does not significantly add to the size of the applicator and does not require disassembly and reassembly for operation.

Another aspect of the invention is to provide an applicator which satisfies all of the foregoing aspects and is easy to fill with fluids, pastes, creams and similar high viscosity materials.

Yet another aspect of the invention is to provide a medicament applicator which is compact, easily storable and transportable, resistant to accidental discharge and moisture evaporation from the medicament, and is easy and inexpensive to manufacture and fill.

SUMMARY OF THE INVENTION

A compact, prefilled, ready-to-use, applicator for dispensing a medicament to a body cavity includes an elongated body having a proximal dispensing end and a distal grasping end. The body is of a sufficient length to dispense medicament to a desired location within a selected body cavity. A proximal portion of the elongated body forms a reservoir adapted to contain a predetermined amount of medicament. A distal portion of the elongated body forms a plunger housing. Closure means are disposed at the dispensing end of the reservoir, and impeller means are disposed at its distal end, at the junction of the reservoir and plunger assembly housing. A telescoping plunger rod assembly, having stop means associated therewith for limiting telescopic extension and preventing telescopic collapse of the plunger rod assembly, is connected to the impeller means. Grasping means are provided for operating said telescoping plunger rod assembly.

The applicator is operated by holding it at the grasping end and inserting it, closure end first, into the desired cavity. The plunger assembly is drawn back via the grasping means to the limit of the stop means, and then the plunger assembly is pushed proximally relative to the elongated body, thereby creating pressure to open the closure member and dispense the medicament from the reservoir.

BRIEF DESCRIPTION OF THE DRAWING

In the accompanying sheets of drawing:

FIG. 1 is a side elevational view of a medicament applicator illustrating the principles of the present invention, shown in the compact, ready-to-use position;

FIG. 2 is an exploded view of the medicament applicator of FIG. 1, showing a closure portion, a cylindrical body portion, a first plunger member and second plunger member (together forming a plunger assembly), and a grasping member;

FIG. 3 is an end view of the closure portion, taken along line 3—3 in FIG. 2;

FIG. 4 is a side view of the closure portion, taken in section along line 4—4 in FIG. 3;

FIG. 5 is an end view of the closure portion, taken in cross-section along line 5—5 in FIG. 1;

FIG. 12 is a side view of an assembled medicament applicator illustrating the principles of the present invention, shown in the compact, ready-to-use position, taken in section along line 12—12 in FIG. 1;

FIG. 13 is another side view, in section, of the medicament applicator of FIG. 12, showing the grasping member and the second plunger member in a position partially drawn back from the first plunger member and the cylindrical body portion, thereby illustrating the operation of a medicament applicator embodying the principles of the present invention;

FIG. 14 is another side view, in section, of the medicament applicator of FIG. 13, showing the grasping member and the second plunger member fully drawn back and engaged with the first plunger member, illustrating a medicament applicator embodying the principles of the present invention in the ready-to-dispense position;

FIG. 15 is another side view, in section, of the medicament applicator of FIG. 14, showing the grasping member and the engaged plunger assembly partially depressed, and the closure portion in the open position for dispensing medicament;

FIG. 16 is another side view, in section, of the medicament applicator of FIG. 15, showing the grasping member and the engaged plunger assembly fully depressed, illustrating a medicament applicator embodying the principles of the present invention after use; and FIG. 17 is a perspective view of a medicament applicator, illustrating the principles of the present invention, shown as properly held in the hand of a user, with the grasping member and second plunger member being partially drawn back.

DETAILED DESCRIPTION OF THE PREFERRED EMBODIMENTS

Figure 6:
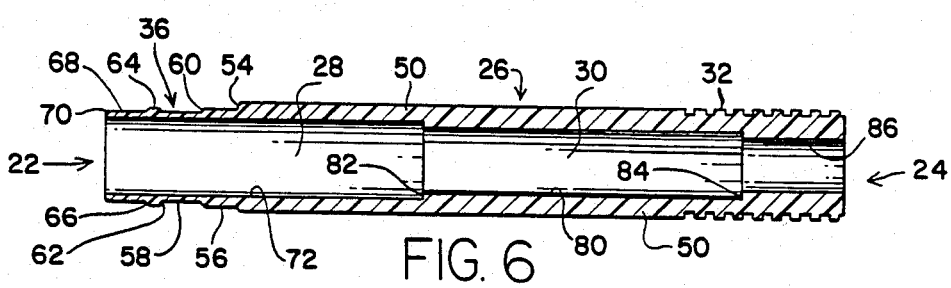
FIG. 6 is a side view of the cylindrical portion, taken in section along line 6—6 in FIG. 2.
Figure 8:
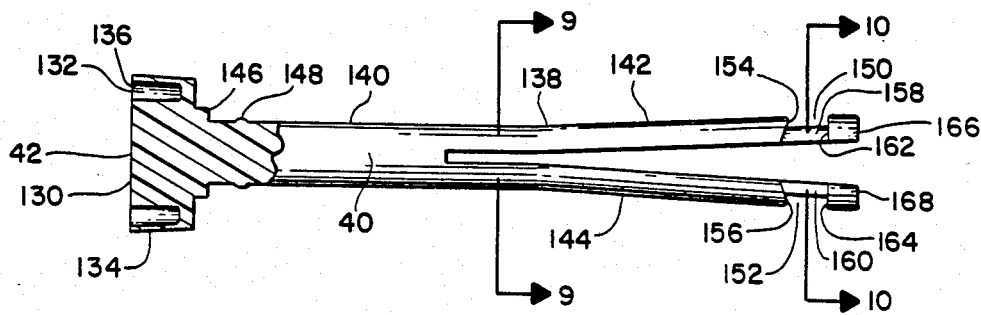
FIG. 8 is a side view of the first plunger member, taken partially in section along line 8—8 in FIG. 7.
Figure 7:
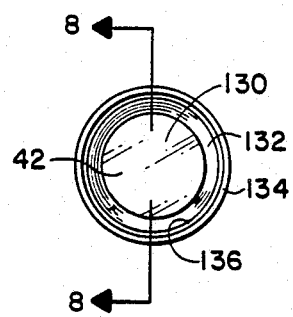
FIG. 7 is a front elevational view of the first plunger member, taken along line 7—7 in FIG. 2.
Figure 9:
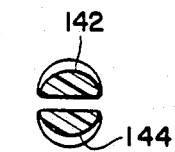
FIG. 9 is an end view of the first plunger member, taken in cross-section along line 9—9 in FIG. 8.
Figure 10:
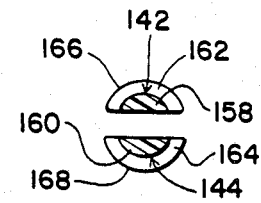
FIG. 10 is an end view of the first plunger member, taken in cross-section along line 10—10 in FIG. 8.
Figure 11:
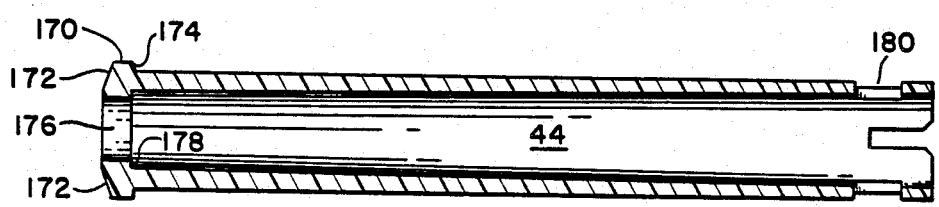
FIG. 11 is a side view of the second plunger member, taken in section along line 11—11 in FIG. 2.

As illustrated in FIGS. 1, 2, 6 and 12, a medicament applicator 20 has a dispensing end 22 and a grasping end 24. A cylindrical member 26 serves as the main body of the applicator, having a medicament reservoir portion 28, a plunger assembly housing portion 30, and a grasping surface portion 32. A closure member 34 is slidingly received over a reduced outer diameter portion 36 of the cylindrical member 26. A plunger assembly 38, having a first plunger member 40 with a piston portion 42 and a second plunger member 44, is slidingly received within cylindrical member 26; the piston portion 42 being disposed within the medicament reservoir portion 28 and the rest of the plunger assembly 38 being disposed within the plunger assembly housing portion 30. A grasping member 46 is provided for the second plunger member 44.

The cylindrical body member 26 is shown as a hollow tube having a series of diameter and wall thickness variations which serve to define various functional aspects of the medicament applicator. The body member need not be cylindrical to fall within the scope of the present invention, but other shapes would entail corresponding modification of the other parts of the medicament applicator. As illustrated in FIG. 6, reduced thickness portion 36 is an annularly recessed portion of outside wall 50 extending over the part of the medicament reservoir portion 28; the amount of diameter reduction is about equal to the wall thickness of the corresponding portion 52 of the closure member 34, so that the overall outside diameter of the medicament applicator 20 remains substantially constant. A rounded ledge 54 cooperates to limit the travel of the closure member toward the grasping end of the applicator. The rounding facilitates comfort during use. Ledge 54 joins outside wall 50 to a first reduced diameter section 56. A second reduced diameter section 58 is connected to first reduced diameter section 56 by a first sloped section 60, and is connected by a second sloped section 62 to an annular retaining ring 64 disposed towards the dispensing end 22. A third sloped section 66 connects ring 64 to a third reduced diameter section 68 which extends to a fourth sloped section 70 at the dispensing end 22 of cylindrical body member 26.

The medicament reservoir portion 28, as defined by an inside wall 72 of the cylindrical portion, has a smooth surface and substantially constant diameter. The plunger assembly housing portion 30, as illustrated in FIG. 6, entails a thickening in the wall 50 of the cylindrical member 26 towards the grasping end 24, and is defined by a reduced diameter portion 80 of inner wall 72 and a first inner ledge 82 located at the boundary with the medicament reservoir portion 28. The first inner ledge 82 prevents the piston portion 42 of plunger assembly 38 from being drawn back into the plunger assembly housing portion when the plunger assembly is extended for use. A second inner ledge 84 is located in the plunger assembly housing portion 30 towards the grasping end 24, and cooperates with the second plunger member 44 to prevent the plunger assembly 38 from being withdrawn from cylindrical body member 26. Second ledge 84 connects to the grasping end 24 of cylindrical member 26 via a second reduced diameter portion 86 of inner wall 72, providing sufficient room for the second plunger member 44 to slide freely.

Turning to FIGS. 3–5, closure member 34 has a rounded end portion 90, a cylindrical portion 92, and a plurality of openings or passages 94 communicating between the medicament reservoir portion 28 and the outside environment for flow of medicament when the applicator 20 is used. Closure member 34 has relatively smooth outer surface 96 and an inner surface 98 having a variety of structural and functional features. The inner surface 98 of rounded end 90 has a series of axially concentric walls 100, 102 and 104 extending slightly into the cylindrical portion 92. Three cross-walls 106 are provided to aid in molding of the closure member 34. Referring now in addition to FIGS. 12 and 13, it can be seen that the outermost concentric wall 104, by extending slightly into cylindrical portion 92 cooperates with the inner surface 98 of the cylindrical portion to securely receive the third reduced diameter section 68 and the fourth sloped section 70 of cylindrical member 26 to provide a moisture-loss-resistant and product retaining barrier.

When positioned on the dispensing end 22 of cylindrical member 26, a first reduced diameter section 110 of the closure member's inner surface 98 is received around and slides on first reduced diameter section 56. An inwardly extending annular ring 112 is connected to reduced diameter section 110 by a first sloped portion 114 and to a second reduced diameter section 116 by a second sloped portion 118, which is in turn connected via a third sloped portion 120 to an inwardly extending portion 122 of the inner surface 98. Retaining ring 112 is received within the second reduced diameter section 58 of the cylindrical member 26 and thereby limits travel of the closure member by the abutment of sloped sections 62 and 118 in the open position and of sloped sections 60 and 114, and 66 and 120, in the closed position. This series of reciprocal thickness changes between the cylindrical member 26 and the closure member 34 restricts movement of the closure member to within a predetermined range, prevents accidental dislodgement of the closure member, and serves as a moisture-loss-resistant barrier for preserving the integrity of the medicament. The use of O-rings and receiving channels therefor is also contemplated as within the scope of the invention for enhancing the prevention of moisture-loss. This arrangement of varied diameter sections helps maintain a moisture-loss-resistant and product retaining seal when the closure is in the storage position. It should be noted however, that for certain more volatile medicaments this arrangement will not give a moisture-proof seal, so additional surrounding moisture proof packaging may be desired.

In the plunger assembly, best illustrated in FIGS. 8–11, the piston portion 42 of the first plunger member has a flattened central portion 130, a recessed portion 132 and an outwardly tapered circumferential edge portion 134. Edge portion 134 is tapered outwardly towards the dispensing end 22 so that when pressure is exerted by the piston on a medicament within the reservoir 28, the back pressure from the medicament will act against a side wall 136 to force edge portion 134 tighter against the inner surface 72 of the reservoir, thereby creating a more positive seal and preventing the loss of medicament.

Behind the piston portion 42, first plunger member has a forked, elongated portion 138 having a solid connecting section 140, a first forked section 142 and a second forked section 144. Solid section 140 has a shoulder portion 146 of a size adapted to fit within the reduced diameter inner wall 80 of cylindrical member 26 at ledge 82, tending to prevent the first piston member from accidentally sliding towards the dispensing end 22 and also acting in part as a seal at the distal end of the reservoir 28. A raised rounded ridge 148 is disposed on solid section 140 to prevent its accidental movement by cooperating with the second plunger member (as will be described later). Each forked section, 142 and 144 has a notched section, 150 and 152, having a sloped forward wall, 154 and 156, a reduced diameter midsection, 158 and 160, and a shoulder, 162 and 164, leading to an enlarged end portion, 166 and 168 (respectively). The first plunger member 40 must be made of a material which is resilient enough to permit compression of the two forked sections 142 and 144 towards each other and respond with restorative force to urge them back away from each other.

Second plunger member 44 is substantially a hollow cylinder with an annularly extending lip 170 having a proximally disposed sloped surface 172 and a distally disposed shoulder 174. The lip 170 also extends inwardly, forming an opening 176 and an inner shoulder 178, designed to hold the second member 44 in a locked position by interaction with ridge 148 on first plunger member 40, but which can easily be pulled past ridge 148, depressing forks 142 and 144 when the second plunger member 44 is drawn back towards the grasping end 24, until it passes the sloped forward walls, 154 and 156, of notches 150 and 152, whereupon forks 142 and 144 spring outward, locking the lip 170 within the notches 150 and 152. By reference to FIG. 14, it can be seen that sloped walls 154 and 156 cooperate with sloped surface 172 to prevent forward slippage, and shoulders 162 and 164 cooperate with shoulder 178 to prevent back slippage. The outer shoulder 174 cooperates with shoulder 84 in cylindrical member 26 to prevent the plunger assembly from being accidentally pulled out from the applicator 20.

Second plunger member 44 has notches 180 at the grasping end to receive corresponding tabs 182 extending from grasping member 46, which is preferably formed in the shape of a ring having an opening 184 for insertion of a finger.

It should be noted that the exploded view of FIG. 2 is not illustrative of the mode of assembly for the applicator. In order to assemble the applicator, the plunger assembly 38 (in its telescopically collapsed or compact position) is inserted, distal end first, into the dispensing end 22 of the main body 26 until the shoulder 146 is received by ledge 82 and the notched end 180 of the second plunger member 44 is in place at the grasping end 24 of the main body (see the position illustrated in FIG. 12). The reservoir portion 28 is filled through the opening at the dispensing end of the main body, either before or after the grasping member 46 has been attached to the notched area 180 of second plunger member 44 (the sequence depends on the medicament filling equipment and procedure that is used). After the reservoir has been filled, the closure member 34 is slid over the reduced outer diameter portion 36, after which time interaction with the retaining ring 64 keeps the closure member from being removed from the main body 26.

Following is a description of the operation of a medicament applicator of the invention, which is provided for use with the reservoir portion 28 prefilled with a desired quantity of a medicament. Essentially, the applicator is inserted, the plunger assembly is extended to lock into engagement and is depressed, then the applicator is withdrawn and discarded. It is, of course, possible to lock the plunger assembly into place before inserting the applicator, but, this would make possible the accidental, premature discharge of medicament during insertion. This would be undesirable because delivery of the medicament at a particular pre-chosen depth within the vagina is preferred.

The applicator 20 is to be hand held, for example by inserting the index finger through the ring opening 184 and by holding the grasping surface 32 between the thumb and remaining fingers (as illustrated in FIG. 17). The dispensing end 22 should be pointed towards the user. The applicator is placed, dispensing end first, into the vaginal orifice and inserted upwards approximately until the grasping surface portion 32 reaches the area surrounding the orifice. The ringed grasping area embodiment shown in the figures is designed to give a tactile indication that the applicator has been inserted to the desired depth for the "average-sized" woman. The depth of such insertion should be kept within the limits of comfort for the user, as there will be variations in vaginal depth.

Once the applicator has been properly inserted, the index finger is extended, causing the grasping member 46 and the second plunger member 44 to be drawn back in the direction of arrows A (illustrated in FIG. 13) until the plunger assembly is fully locked into telescopically extended engagement between its members (illustrated in FIG. 14). The first and second forked sections, 142 and 144, will have spread so that inner area 176 of the second plunger member is firmly seated within notches 150 and 152. The index finger is then flexed, driving the plunger assembly 38 toward the dispensing end 22 (see arrow B), causing pressure to be exerted (see arrows C) on the closure member 34 which in turn slides forward (see arrows D) opening the seal formed by wall 104, surface 98 and the body member 26, allowing the medicament to flow (see arrows E) through openings 94 and into the vagina (illustrated in FIG. 15). The plunger assembly should be pressed forward until the grasping member 46 contacts the cylindrical body member 26 (illustrated in FIG. 16) at which point substantially all of the medicament will have been dispensed (leaving less than about 10% residue). At that time, the applicator 20 should be withdrawn and may be discarded.

It should be noted that the medicament applicator of the present invention can be employed to deliver medicaments to body cavities other than the vagina, for example the anus, or the deliver medicaments to locations other than the inside of body cavities. It can also be used to dispense fluids, pastes, creams and other low viscosity materials. It may, however, be desired to modify the diameter of the applicator for such other uses. Also, the medicament applicator of the present invention is not limited to use in human beings, and could be used for delivering medication to animals (one example being the delivery of worming medicine to horses). The preferred use, however, is as a vaginal applicator for medicament creams.

While this invention has been described with reference to specific embodiments thereof, it should be understood by those skilled in this art that various changes may be made and equivalents may be substituted without departing from the true spirit and scope of the invention. For example, the shape of the main body could be varied as can its length and diameter. other types of grasping surfaces could be used. Furthermore, the plunger assembly and the closure of the invention could be employed with medicament applicators other than the applicator described in the preferred embodiments. Thus, the various novel elements as described herein, can be used individually or collectively, as desired. All such modifications are intended to be within the scope of the claims appended hereto. .

What is claimed is:

1. A telescoping rod assembly for prefilled syringes, medicament applicators and the like, said telescoping rod assembly comprising:
 a first rod member comprising:
  a first portion having a continuous circumferential surface, and
  a second portion comprising two forks extending from said first portion at an angle;
 a second rod member slidingly associated with said first rod member; and
 engaging means comprising reciprocal protruding and receding portions,
  said receding portion of said engaging means being disposed inwardly from an outwardly facing surface of said second portion of said first rod member, and
  said protruding portion of said engaging means being disposed on said second rod member;
 said forks being adapted to spring outward upon alignment of said protruding portion with said receding portion to lock said engaging means.

2. The telescoping rod assembly of claim 1, wherein:
 said first rod member is at least partially receivable within said second rod member,
 said forks are angled outward, towards said second rod member and,
 said forks are compressable towards each other when said second portion of said first rod member is received within said second rod member.

3. The telescoping rod assembly of claim 2, wherein:
 said receding portion of said engaging means comprises a recess disposed towards the end of each of said forks farthest from said first portion of said first rod member, and
 said protruding portion of said engaging means comprises a shoulder disposed inwardly about a first end of said second rod member;
whereby, upon extending said first and second rod members, said shoulder is received in said recesses to engage said first and second rod members together.

4. The telescoping rod assembly of claim 3, wherein said engaging means comprises:
 a sloped wall at an end of said recess closest to said first portion of said first rod member, and
 a reciprocally sloped end wall on said first end of said second rod member, said sloped end walls being so oriented as to prevent disengagement of said forks from said second rod member upon compression of said engaged first and second rod members together.

5. An automatically-openable closure for a medicament applicator, said closure comprising:
a proximal blunted end portion for facilitating penetration into a body cavity;
a cylindrical portion extending distally from said blunted end portion;
at least one opening through said closure, said opening being disposed near the junction of said blunted end portion and said cylindrical portion;
an annular wall extending inside said cap distally from said blunted proximal end portion beyond said opening,
said annular wall being substantially coaxial with and separated from said cylindrical portion by a distance slightly less than the wall thickness of the proximal portion of the medicament applicator about which said closure is to be disposed;
said blunted end portion, said annular wall and said cylindrical portion together forming a space for snugly receiving an end of the proximal portion of the medicament applicator about which said closure is to be disposed; and
motion limiting means for restricting the proximal sliding motion of said automatically-openable closure with respect to the medicament applicator about which said closure is to be disposed.

6. The automatically-openable closure of claim 5 wherein said motion limiting means comprises an annularly raised portion disposed inwardly on said cylindrical portion to cooperate with an outward annularly raised portion of the medicament applicator about which said closure is to be disposed, to permit assembly of said closure by sliding said cylindrical portion over the proximal end of the medicament applicator about which said closure is to be disposed, and to prevent said closure from subsequently being disassembled from such medicament applicator.

7. A medicament applicator comprising:
an elongated body member having a proximal dispensing end and a distal grasping end, said body member being of sufficient length to dispense medicament to a desired location with a body cavity;
a reservoir formed by a proximal portion of said elongated body member, said reservoir being adapted to contain a predetermined amount of medicament;
impeller means disposed towards the distal end of said reservoir;
a telescoping rod assembly disposed within a distal portion of said elongated body member, a proximal end of said rod assembly being connected to said impeller means,
engaging means for limiting telescopic extension and preventing telescopic collapse of said rod assembly;
grasping means disposed at a distal end of said telescoping rod assembly; and
closure means slidably disposed on said elongated body member at said proximal dispensing end, said closure means being proximally slidable when acted upon by a fluid under pressure from said impeller means, from a distal, closed position to a proximal, open position, said closure means remaining on said elongated body member when in said open position.

8. The medicament applicator of claim 7, wherein said rod assembly comprises:
a first rod member comprising:
a first portion having a continuous circumferential surface, and
a second portion comprising two forks extending from said first portion at an angle; and
a second rod member slidingly associated with said first rod member;
said engaging means comprising reciprocal protruding and receding portions,
said receding portion of said engaging means being disposed inwardly from an outwardly facing surface of said second portion of said first rod member, and
said protruding portion of said engaging means being disposed on said second rod member.

9. The medicament applicator of claim 8, wherein:
said first rod member is at least partially receivable within said slecond rod member,
said forks are angled outward, towards said second rod member,
said forks are compressable towards each other when said second portion of said first rod member is received within said second rod member, and
said forks are adapted to spring outward upon alignment of said protruding portion with said receding portion to lock said engaging means.

10. The medicament applicator of claim 9, wherein:
said first portion of said first rod member is disposed towards the proximal end of said elongated body member;
said receding portion of said engaging means comprises a recess disposed towards the distal end of each of said forks;
said protruding portion of said engaging means comprises a shoulder disposed inwardly about a proximal end of said second rod member;
the proximal end of said first rod member being connected to said impeller means; and
the distal end of said second rod member being connected to said grasping means; whereby, upon extending said second rod member distally, said shoulder is received in said recesses to engage said first and second rod members together.

11. The medicament applicator of claim 10, wherein said engaging means comprises:
a sloped wall at the proximal end of each said recess, and
a reciprocally sloped wall at the proximal end of said second rod member;
said sloped walls being so oriented as to prevent disengagement of said forks from said second rod member upon proximal movement of said rod assembly.

12. The medicament applicator of claim 8, wherein said grasping means comprises a ring for operating said telescoping rod assembly.

13. The medicament applicator of claim 9, wherein:
said first portion of said first rod member is disposed towards the distal end of said elongated body member;
said receding portion of said engaging means comprises a recess disposed towards the proximal end of each of said forks;
said protruding portion of said engaging means comprises a shoulder disposed inwardly about a distal end of said second rod member;

the distal end of said first rod member being connected to said grasping means; and the proximal end of said second rod member being connected to said impeller means;

whereby, upon extending said first rod member distally, said shoulder is received in said recesses to engage said first and second rod members together.

14. The medicament applicator of claim 13, wherein said engaging means comprises:

a sloped wall at the distal end of said recess, and a reciprocally sloped end wall on said distal end of said second rod member;

said sloped end walls being oriented so as to prevent disengagement of said forks from said second rod member upon proximal movement of said rod assembly.

15. The medicament applicator of claim 7 wherein said telescoping rod assembly comprises a first rod member received within a second rod member; and wherein said engaging means comprises:

at least one tab associated with one of said rod members and extending towards said other rod member, and at least one reciprocal slot associated with said other rod member to receive said tab.

16. The medicament applicator of claim 7, wherein said grasping means comprises a ring for operating said telescoping rod assembly.

17. The medicament applicator of claim 7, wherein said closure means comprises a cap having:

a proximal blunted end portion for facilitating penetration into a body cavity;

a cylindrical portion extending distally from said blunted end portion;

at least one opening through said cap, said opening being disposed near the junction of said blunted end portion and said cylindrical portion;

an annular wall extending distally inside said cap, from said blunted proximal end portion beyond said opening, said annular wall being substantially coaxial with and separated from said cylindrical portion by a distance slightly less than the wall thickness of said proximal portion of said elongated body member about which said closure means is slidably disposed, said blunted end portion, said annular wall and said cylindrical portion together forming a space for receiving an end of said proximal portion of said elongated body member; and motion limiting means for restricting the proximal sliding motion of said cap with respect to said elongated body member.

18. The medicament applicator of claim 8, wherein said closure means comprises a cap having:

a proximal blunted end portion for facilitating penetration into a body cavity;

a cylindrical portion extending distally from said blunted end portion;

at least one opening through said cap, said opening being disposed near the junction of said blunted end portion and said cylindrical portion;

an annular wall extending distally inside said cap, from said blunted proximal end portion beyond said opening, said annular wall being substantially coaxial with and separated from said cylindrical portion by a distance slightly less than the wall thickness of said proximal portion of said elongated body member about which said closure means is slidably disposed, said blunted end portion, said annular wall and said cylindrical portion together forming a space for receiving an end of said proximal portion of said elongated body member; and motion limiting means for restricting the proximal sliding motion of said cap with respect to said elongated body member.

19. The medicament applicator of claim 7, comprising a second grasping means formed as a roughened exterior surface disposed distally on said elongated body member.

20. The medicament applicator of claim 7, wherein said elongated body member has a non-uniform outside diameter.

21. The medicamenft applicator of claim 7, wherein said closure means is slidably disposed about a reduced diameter portion of said proximal dispensing end of said elongated body member and has an outside diameter substantially the same as the outside diameter of that portion of the proximal dispensing end of said elongated body member which is adjacent to said closure means when said closure means is in the closed position.

22. An applicator for dispensing a medicament, said applicator comprising:

an elongated body member having a proximal dispensing end and a distal grasping end, said body member being of sufficient length to dispense medicament at a desired location within a selected body cavity;

a proximal portion of said elongated body member forming a reservoir adapted to contain a predetermined amount of medicament; and a distal portion of said elongated body member forming a plunger assembly housing;

closure means disposed at said proximal dispensing end, said closure means being slidingly received over a reduced wall thickness portion of said elongated body member, said portion being defined by an inwardly extending shoulder disposed towards the proximal end of said body member, said closure means comprising:

a blunted proximal portion for facilitating penetration into a body cavity;

a cylindrical portion extending distally from said blunted end portion;

at least one opening through said closure means, said opening being disposed near the junction of said blunted proximal portion and said distal cylindrical portion, a circular member, extending distally inside said closure from said blunted proximal portion beyond said opening and at least partly into an area surrounded by said cylindrical portion, said circular member being substantially coaxial with said cylindrical portion; and motion limiting means for restricting the sliding motion of said closure with respect to a medicament applicator with which it is employed, said motion limiting means retaining said closure against said applicator to effect a seal until delivery pressure is exerted on a medicament in the applicator and exceeds the force of the motion limiting means, moving the closure proximally and out of sealing relationship with said medicament applicator, thereby opening a channel to flow of medicament through said opening, said motion limiting means comprising:
    a first annular raised portion extending outwardly from said reduced wall thickness portion of said body member,
    a second annular raised portion extending inwardly from said cylindrical portion of said closure means, and
    said shoulder;
    said first and second annular raised portions cooperating to limit proximal sliding of said closure means, and said shoulder cooperating with the distal terminal end of said cylindrical portion to limit distal sliding of said closure means;

impeller means disposed at the distal end of said reservoir;

a telescoping rod assembly, a proximal end of said rod assembly being connected to said impeller means, said rod assembly having engaging means associated therewith for limiting telescopic extension and preventing telescopic collapse of said rod assembly; and grasping means for operating said telescoping rod assembly;

wherein said applicator is operated by holding the grasping end of said body member and inserting the body member into the desired cavity, drawing said rod assembly via said grasping means distally to the limit of the engaging means and then pushing said rod assembly proximally, thereby creating pressudre to open said closure means and to dispense the medicament from the reservoir.

23. The medicament applicator of claim 22 wherein said shoulder and said distal terminal end of said cylindrical portion are rounded.

24. The medicament applicator of claim 22 comprising an second reduced thickness portion between said shoulder and said reduced wall thickness portion, whereby the distal portion of said cylindrical portion is slidingly received on said second reduced thickness portion to maintain said main body and said cylindrical portion substantially parallel to each other throughout the sliding motion of said closure means.

25. The medicament applicator of claim 24 wherein said second annular raised portion is disposed between said first annular raised portion and said second reduced thickness portion.

26. An applicator for dispensing a medicament, said applicator comprising:
    an elongated body member having a proximal dispensing end and a distal grasping end, said body member being of sufficient length to dispense medicament at a desired location within a selected body cavity;
    a proximal portion of said elongated body member forming a reservoir adapted to contain a predetermined amount of medicament; and
    a distal portion of said elongated body member forming a plunger assembly housing;
    closure means disposed at said proximal dispensing end, said closure means being slidingly received over a reduced wall thickness portion of said elongated body member, said portion being defined by an inwardly extending shoulder disposed towards the proximal end of said body member, said closure means comprising:
        a blunted proximal portion for facilitating penetration into a body cavity;
        a cylindrical portion extending distally from said blunted end portion;
        at least one opening through said closure means, said opening being disposed near the junction of said blunted proximal portion and said distal cylindrical portion,
        a circular member, extending distally inside said closure from said blunted proximal portion beyond said opening and at least partly into an area surrounded by said cylindrical portion, said circular member being substantially coaxial with said cylindrical portion; and
    motion limiting means for restricting the sliding motion of said closure with respect to a medicament applicator with which it is employed, said motion limiting means retaining said closure against said applicator to effect a seal until delivery pressure is exerted on a medicament in the applicator and exceeds the force of the motion limiting means, moving the closure proximally and out of sealing relationship with said medicament applicator, thereby opening a channel to flow of medicament through said opening, said motion limiting means comprising:
        a first annular raised portion extending outwardly from said reduced wall thickness portion of said body member,
        a second annular raised portion extending inwardly from said cylindrical portion of said closure means, and
        said shoulder;
        said first and second annular raised portions cooperating to limit proximal sliding of said closure means, and said shoulder cooperating with the distal terminal end of said cylindrical portion to limit distal sliding of said closure means;

impeller means disposed at the distal end of said reservoir;

a telescoping rod assembly, a proximal end of said rod assembly being connected to said impeller means, said rod assembly having engaging means associated therewith for limiting telescopic extension and preventing telescopic collapse of said rod assembly,
    said rod assembly comprising:
        a first rod member and a second rod member, said first and second rod members being slidingly associated with each other; said engaging means comprising:
        a first engaging means associated on a distal portion of one of said rod members engagable with a second engaging means associated on a proximal portion of said other rod member; and grasping means for operating said telescoping rod assembly;

wherein said applicator is operated by holding the grasping end of said body member and inserting the body member into the desired cavity, drawing said rod assembly via said grasping means distally to the limit of the engaging means and then pushing said rod assembly proximally, thereby creating pressure to open said closure means and to dispense the medicament from the reservoir.

27. The medicament applicator of claim 26 wherein said shoulder and said distal terminal end of said cylindrical portion are rounded.

28. The medicament applicator of claim 26 wherein said first and second annular raised portions cooperate to permit assembly of said closure over the proximal end of said body member, and to prevent said closure member from subsequently being disassembled from said body member.

29. The medicament applicator of claim 22 comprising a second reduced thickness portion between said shoulder and said reduced wall thickness portion, whereby the distal portion of said cylindrical portion is slidingly received on said second reduced thickness portion to maintain said main body and said cylindrical portion substantially parallel to each other throughout the sliding motion of said closure means.

30. The medicament applicator of claim 29 wherein said second annular raised portion is disposed between said first annular raised portion and said second reduced thickness portion.

* * * * *